United States Patent [19]

Schaar

[11] 4,265,234
[45] May 5, 1981

[54] DRESSING COMPOSITE

[75] Inventor: Charles H. Schaar, Lake Zurich, Ill.

[73] Assignee: The Kendall Company, Boston, Mass.

[21] Appl. No.: 93,956

[22] Filed: Nov. 14, 1979

[51] Int. Cl.³ .............................................. A61F 15/00
[52] U.S. Cl. ..................................... 128/156; 206/441
[58] Field of Search ............................... 128/155–156; 206/339, 440–441, 813, 828

[56] References Cited

U.S. PATENT DOCUMENTS

| 2,703,083 | 3/1955  | Gross ........................... 128/156 |
| 2,721,550 | 10/1955 | Banff ........................... 128/156 |
| 2,836,178 | 5/1958  | Barr ............................ 128/155 |
| 2,924,331 | 2/1960  | Hoey ........................... 206/441 |
| 3,313,405 | 4/1967  | Blackford ..................... 206/441 |
| 3,612,265 | 10/1971 | Dickerson ..................... 206/441 |
| 4,094,316 | 6/1978  | Nathanson ..................... 128/156 |
| 4,161,176 | 7/1979  | Harris et al. .................. 128/155 |

FOREIGN PATENT DOCUMENTS

| 1254818 | 11/1967 | Fed. Rep. of Germany ........... 128/155 |
| 2409210 | 7/1979  | France ........................ 128/155 |

Primary Examiner—C. Fred Rosenbaum
Attorney, Agent, or Firm—Powell L. Sprunger

[57] ABSTRACT

A dressing composite comprising, a bandage comprising an elongated backing sheet having a back surface facing away from a patient after application of the bandage, a front surface facing toward the patient after application of the bandage, an absorbent pad located over the front surface of the backing sheet and intermediate opposed ends of the backing sheet, and an adhesive covering a substantial portion of the front surface of the backing sheet intermediate the pad and the opposed ends of the backing sheet. The dressing composite has a package comprising a front cover sheet extending the length of the bandage, and having a width greater than the width of the bandage backing sheet, with opposed side margins of the front cover sheet extending past opposed sides of the bandage, and an inner release surface releasably attached to the exposed adhesive of the bandage. The dressing composite has a back cover sheet extending the length of the bandage, and having a width greater than the width of the bandage backing sheet, with opposed side margins of the back cover sheet extending past opposed sides of the bandage, and an adhesive on a front surface of the back cover sheet with a portion of the adhesive being releasably attached to the back surface of the backing sheet, and a portion of the adhesive extending along the side margins on the front surface of the back cover sheet and being releasably attached to a release surface on the side margins of the facing inner surface of the front cover sheet. The front and back cover sheets are releasably attached together adjacent at least one end of the bandage.

10 Claims, 6 Drawing Figures

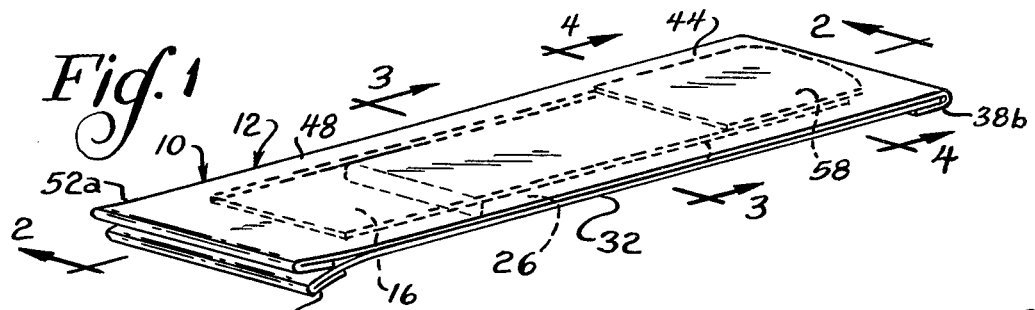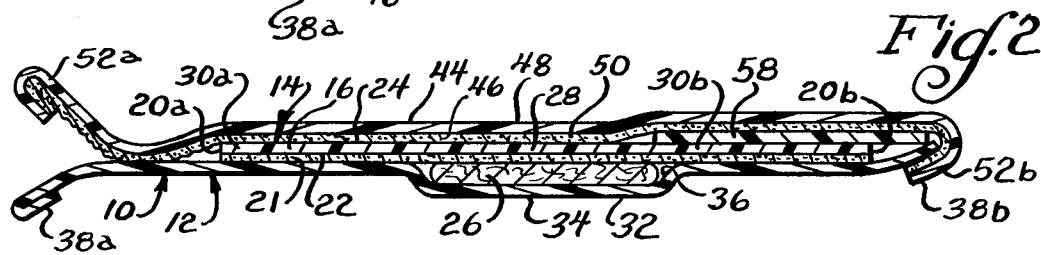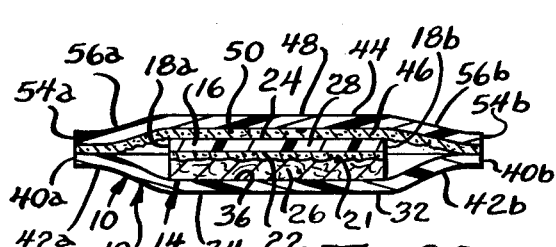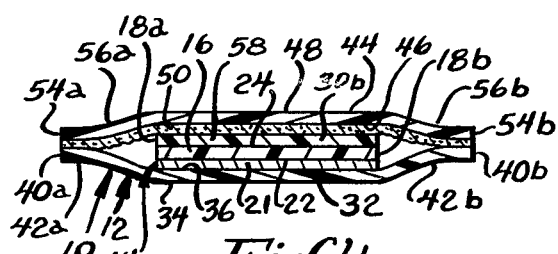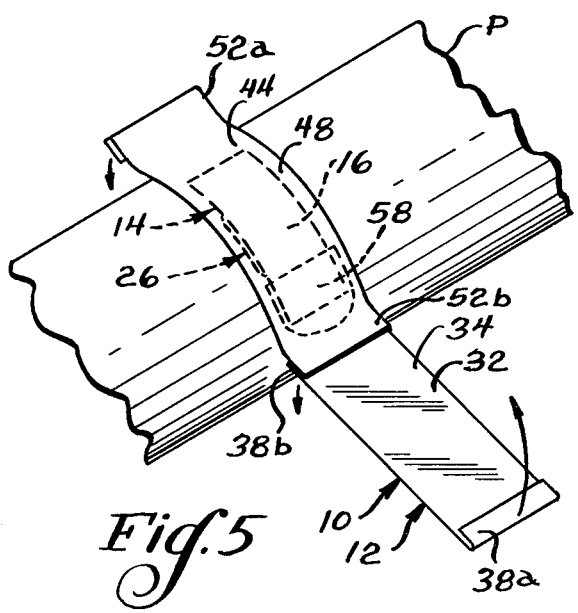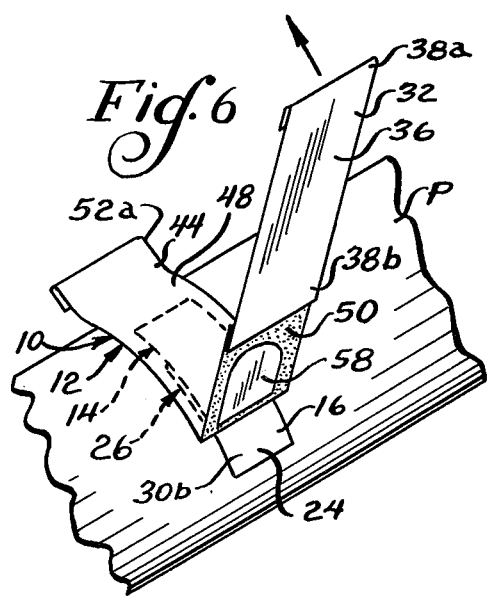

DRESSING COMPOSITE

BACKGROUND OF THE INVENTION

The present invention relates to dressing composites, and more particularly to packaged bandages.

Before the present invention, bandages have been commonly supplied to the consumer in paper packages which are opened to expose the bandage at the time of use. The bandage normally have an absorbent pad, and opposed end portions with adhesive for attaching the bandage to the patient. However, the packaged bandages have required separate release sheets for the adhesive on the bandage end portions, which must be removed from the bandage and discarded when it is desired to apply the bandage, thus causing inconvenience to the user and unduly complicating the attachment procedure.

SUMMARY OF THE INVENTION

The principal feature of the present invention is the provision of an improved dressing composite of simplified construction.

The dressing composite has a bandage comprising an elongated backing sheet having a back surface facing away from a patient after application of the bandage, a front surface facing toward the patient after application of the bandage, and absorbent pad located over the front surface of the backing sheet and intermediate opposed ends of the backing sheet, and an adhesive covering a substantial portion of the front surface of the backing sheet intermediate the pad and the opposed ends of the backing sheet. The dressing composite has a package comprising a front cover sheet extending the length of the bandage, and having a width greater than the width of the bankdage backing sheet, with opposed side margins of the front cover sheet extending past opposed sides of the bandage, and an inner release surface releasably attached to the exposed adhesive of the bandage. The dressing composite also has a back cover sheet extending the length of the bandage, and having a width greater than the width of the bandage backing sheet, with opposed side margins of the back cover sheet extending past opposed sides of the bandage, and an adhesive on a front surface of the back cover sheet with a portion of the adhesive being releasably attached to the back surface of the backing sheet, and a portion of the adhesive extending along the side margins on the front surface of the back cover sheet and being releasably attached to a release surface on the side margins of the facing inner surface of the front cover sheet. The dressing composite also has means for releasably attaching the front and back cover sheets together adjacent at least one end of the bandage.

A feature of the present invention is that the front and back cover sheets may be separated adjacent the one end of the bandage, and the front cover sheet may be peeled from the back cover sheet and bandage to expose the adhesive on the bandage for attachment to the patient.

Another feature of the invention is that the adhesive on the back cover sheet attached to the bandage backing sheet retains the bandage to the back cover sheet while the front cover sheet is peeled from the bandage.

Yet another feature of the invention is that the adhesive on the back cover sheet attached to the bandage backing sheet retains the bandage in place on the package to facilitate attachment of the bandage to the patient through use of the package with the adhesive on the bandage exposed.

Still another feature of the invention is that the back cover sheet may be readily removed from the bandage after attachment of the bandage to the patient.

A further feature of the invention is that the back cover sheet may be free of attachment from the bandage backing sheet in a region adjacent the other end of the bandage to facilitate removal of the back cover sheet from the bandage backing sheet.

Another feature of the invention is that the dressing composite eliminates the necessity for separate release sheets to cover the adhesive on the bandage.

Yet another feature of the invention is that the front and back cover sheets may be joined together adjacent the other end of the bandage, such that only the single package need be discarded after application of the bandage, rather than a pair of release sheets and a separate package.

Thus, a feature of the invention is that the dressing composite greatly facilitates attachment of the bandage to the patient in a convenient and simplified manner.

Further features will become more fully apparent in the following description of the embodiments of this invention and from the appended claims.

DESCRIPTION OF THE DRAWINGS

In the drawings:

FIG. 1 is a perspective view of a dressing composite of the present invention;

FIG. 2 is a sectional view taken substantially as indicated along the line 2—2 of FIG. 1;

FIG. 3 is a sectional view taken substantially as indicated along the line 3—3 of FIG. 1;

FIG. 4 is a sectional view taken substantially as indicated along line 4—4 of FIG. 1; and FIGS. 5 and 6 are perspective views illustrating use of the dressing composite for attaching a bandage in the composite to a patient.

DESCRIPTION OF THE PREFERRED EMBODIMENTS

Referring now to FIGS. 1-4, there is shown a dressing composite generally designated 10 comprising a package 12, and a bandage 14 retained in the package 12. The bandage 14 has a backing sheet 16 having a pair of opposed side edges 18a and 18b, a pair of opposed end edges 20a and 20b connecting the side edges 18a and b, a front surface 22 facing toward the patient after application of the bandage 14, and a back surface 24 facing away from the patient after application of the bandage 14. As shown, the bandage 14 has a pressure-sensitive adhesive 21 of suitable type covering the front surface 22 of the backing sheet 16, and an absorbent pad 26 for placement over a patient's wound, such as a pad of the type disclosed in U.S. Pat. No. 2,923,298, incorporated herein by reference, with the pad 26 being secured by the adhesive 21 to a central portion 28 of the backing sheet 16, such that a pair of opposed end portions 30a and 30b of the backing sheet 16 are defined intermediate the pad 26 and associated end edges 20a and b, respectively, with the end portions 30a and b of the backing sheet 16 having adhesive 21 on opposed sides of the pad 26 for attachment of the bandage 14 to the patient with the pad 26 located over the patient's wound. The backing sheet 16 may be constructed of a suitable material, such as a plastic material with a back surface having a relatively low affinity for adhesive on the package 12, as described below, or a suitable flexible material, such as a nonwoven or paper material, which may be treated to form a release back surface 24, such as by silicone.

The package 12 has an elongated front cover sheet 32 having a length greater than the length of the bandage backing sheet 16, and a width greater than the width of the bandage 14. The front cover sheet 32 has an outer surface 34 facing away from the bandage 14 in the package, and an inner surface 36 facing toward the bandage in the package. The front cover sheet 32 may be constructed from a suitable material, such as plastic, defining a release inner surface 36, or may be constructed from a suitable material, such as paper, which is treated in a suitable manner, such as by silicone, to define a release inner surface 36 for releasable attachment of the surface 36 to the adhesive 21 on the bandage 14 and the adhesive subsequently to be described on a back cover sheet of the package 12, with the release portion of the inner surface 36 preferable extending the length and width of the front cover sheet 32. The front cover sheet 32 has a pair of opposed end portions 38a and 38b, and a pair of opposed side edges 40a and 40b defining elongated opposed side margins 42a and 42b extending past the side edges 18a and b of the bandage 14. If desired, the outer end portion 38a may be doubled together in suitable manner to form a tab, such as through use of adhesive on the outer surface 34 of the folded over end portion 38a.

The package 12 also has a back cover sheet 44 having a length greater than the length of the backing sheet 16 of the bandage 14, and a width greater than the width of the bandage 14. The back cover sheet 44 has a front surface 46 facing toward the back surface 24 of the bandage backing sheet 16, and a back surface 48 facing away from the back surface 24 of the bandage backing sheet 16. As shown, the back cover sheet 44 has a pressure sensitive adhesive 50 of suitable type on the front surface 46 of the back cover sheet 44, and, in a preferred form, the adhesive 50 extends the length and width of the back cover sheet 44. The back cover sheet 44 has a pair of opposed end portions 52a and 52b, with the end portion 52b of the back cover sheet 44 overlapping the end portion 38b of the front cover sheet 32, such that the adhesive on the end portion 52b is fixedly attached to the outer surface 34 of the end portion 38b to connect the front cover sheet 32 to the back cover sheet 44 in the region of the overlapped end portions 38b and 52b. If desired, the end portion 52a of the back cover sheet 44 may be folded over to form a tab, with the adhesive 50 of the back cover sheet maintaining the folded over end portion in place.

The back cover sheet 44 has a pair of opposed side edges 54a and 54b defining opposed side margins 56a and 56b extending past the side edges 18a and b of the bandage backing sheet 16. Thus, the adhesive 50 on the back cover sheet side margins 56a and b is releasably attached to the release inner surface 36 of the front cover sheet side margins 42a and b in order to releasably close the package on opposed sides of the bandage 14. Also, the adhesive 50 on the backing sheet end portion 52a is releasably attached to the release inner surface 36 of the front cover sheet end portion 38a in order to releasably close one end of the package 12 adjacent the end edge 20a of the backing sheet 16, while the secured end portions 38b and 52b of the front cover sheet 32 and back cover sheet 34, respectively, close the other end of the package adjacent the end edge 20b of the bandage backing sheet 16. Thus, in this manner, the adhesive 50 on the back cover sheet 44 and the release inner surface 36 of the front cover sheet 32 are utilized to form a closed sterile package 12 for the bandage 14.

As shown, the back cover sheet 44 has an elongated barrier sheet 58 secured to the adhesive 50 intermediate the adhesive 50 and the back surface 24 of the bandage backing sheet 16, with the barrier sheet 58 extending from the end edge 20b longitudinally along the backing sheet 16 toward the central location of the pad 26, and with the barrier sheet 58 having a width approximately equal to the width of the backing sheet 16. In this manner, the barrier sheet 58 prevents adhesion of the back cover sheet 44 to the backing sheet 16 of the bandage 14 in an elongated region of the bandage end portion 30b adjacent the end edge 20b for a purpose which will be described below. Alternatively, the back cover sheet 44 may be formed free of adhesive in the region otherwise occupied by the barrier sheet 58 to prevent adhesion of the back cover sheet 44 to the back surface 24 of the backing sheet 16 in the specified region without use of the barrier sheet 58.

In use, the end portions 38a and 52a of the front cover sheet 32 and the back cover sheet 44, respectively, are gripped by the user to peel the end portion 38a from the end portion 52a, and peel the side margins 42a and b of the front cover sheet 32 fron the side margins 56a and b of the back cover sheet 44 to expose the absorbent pad 26 and the adhesive 21 on the bandage end portions 30a and b. In this configuration, the front cover sheet 32 has been removed from the back cover sheet 44, with the exception of the end portions 38b and 52b which remain attached, while the adhesive 50 retains the bandage backing sheet 16 in place on the back cover sheet 44. Thus, with reference to FIG. 5, the back cover sheet 44 may be grasped by the user in order to locate the bandage pad 26 over the patient's wound, and the back cover sheet 44 may be pressed along its length in order to apply pressure to the bandage end portions 30a and b and secure the bandage 14 in place on the patient P by the adhesive 21 on the end portions 30a and b. With reference to FIG. 6, once the bandage has been secured to the patient, the front cover sheet 32 may be grasped by the user and pulled outwardly from the bandage backing sheet 16 in order to peel the adhesive 50 from the back surface 24 of the backing sheet 16 and thus remove the package 12 from the bandage 14, with the barrier sheet 58 preventing adhesion of the back cover sheet 44 to the bandage backing sheet 16 in the described region of the end portion 30b to facilitate initial peeling of the back cover sheet 44 from the bandage backing sheet 16.

Thus, in accordance with the present invention, the adhesive 50 of the back cover sheet 44 and the release inner surface 36 of the front cover sheet 32 cooperate to define a closed package 12 for the bandage 14 which may be peeled apart to expose the front of the bandage 14 at the time of use. Also, the adhesive 50 of the back cover sheet 44 maintains the bandage 14 in place during application of the bandage to facilitate the application procedure. Moreover, the back cover sheet 44 may be readily removed from the bandage 14 after placement on the patient, and the removed package may be discarded in a single piece after the back cover sheet 44 has been removed from the bandage backing sheet 16. Thus, the dressing composite of the present invention eliminates the necessity of separate release sheets for the bandage which must be removed and discarded at the time of use, in addition to a conventional package which normally covers the bandage, and the dressing composite thus facilitates and simplifies application of the bandage, as well as eliminates the necessity for discarding additional components, such as release sheets, after application of the bandage.

The foregoing detailed description is given for clearness of understanding only, and no unnecessary limitaions should be understood therefrom, as modifications will be obvious to those skilled in the art.

I claim:

1. A dressing composite, comprising:
   a bandage comprising a backing sheet having a back surface facing away from a patient after application of the bandage, a front surface facing toward the patient after application of the bandage, an absorbent pad located over the front surface of said backing sheet and intermediate opposed ends of the backing sheet, and an adhesive covering a substantial portion of the front surface of the backing sheet intermediate said pad and the opposed ends of the backing sheet; and
   a package comprising a front cover sheet extending the length of the bandage, and having a width greater than the width of the bandage backing sheet, with opppsed side margins of the front cover sheet extending past opposed sides of the bandage, and an inner release surface releasably attached to the exposed adhesive of the bandage, and a back cover sheet extending the length of the bandage, and having a width greater than the width of the bandage backing sheet, with opposed side margins of the back cover sheet extending past opposed sides of the bandage, an adhesive on the back cover sheet extending along the side margins of the back cover sheet and being releasably attached to a release surface on the facing side margins of the front cover sheet, and means for releasably attaching said front and back cover sheets together adjacent at least one end of the bandage, the adhesive on the back cover sheet includes a substantial portion on a front surface of the back cover sheet releasably attached to the back surface of the backing sheet and a portion on the front surface of the back cover sheet side margins releasably attached to the facing inner release surface of the front cover sheet side margins, said back cover sheet being free of attachment from the back surface of the bandage backing sheet in an elongated region extending from the other end of the bandage toward the one end of the bandage.

2. The dressing composite of cliam 1 wherein said pad is generally centrally located intermediate the opposed ends of said backing sheet.

3. The dressing composite of claim 1 wherein said pad is secured to the backing sheet by said adhesive on the front surface of the backing sheet.

4. The dressing composite of claim 1 wherein said front and back cover sheets are connected adjacent the other end of said bandage.

5. The dressing composite of claim 4 wherein the adhesive on the back cover sheet extends throughout at least a portion of said region, and including a barrier sheet secured to and covering the adhesive in said region to prevent attachment of the adhesive on the back cover sheet to the bandage backing sheet in said region.

6. The dressing composite of claim 1 wherein said front and back cover sheets are separate, and including means for joining the front and back cover sheets together adjacent the other end of said bandage.

7. The dressing composite of claim 6 wherein the joining means comprises adhesive on the front surface of an end margin of the back cover sheet overlapping and secured to an outer surface of an end margin of the front cover sheet.

8. The dressing composite of claim 1 wherein the adhesive on the back cover sheet covers at least substantially the entire front surface of the back cover sheet.

9. The dressing composite of claim 1 wherein the attaching means comprises an area of adhesive on the front surface of the back cover sheet extending past one end of the bandage, and an inner release surface area of the front cover sheet being releasably attached to said adhesive area.

10. The dressing composite of claim 1 wherein said front and back cover sheets include end portions extending past said attaching means and being free of attachment to facilitate removal of the front cover sheet from the back cover sheet.

* * * * *